US011278889B2

(12) United States Patent
Donaldson et al.

(10) Patent No.: US 11,278,889 B2
(45) Date of Patent: Mar. 22, 2022

(54) TEST SAMPLE DEVICES AND METHODS

(71) Applicant: HEWLETT-PACKARD DEVELOPMENT COMPANY, L.P., Spring, TX (US)

(72) Inventors: Jeremy Harlan Donaldson, Corvallis, OR (US); Stephen Lee Frey, Corvallis, OR (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 134 days.

(21) Appl. No.: 16/616,944

(22) PCT Filed: Jul. 18, 2017

(86) PCT No.: PCT/US2017/042599
§ 371 (c)(1),
(2) Date: Nov. 25, 2019

(87) PCT Pub. No.: WO2019/017912
PCT Pub. Date: Jan. 24, 2019

(65) Prior Publication Data
US 2020/0164371 A1    May 28, 2020

(51) Int. Cl.
*B01L 3/00*    (2006.01)

(52) U.S. Cl.
CPC ..... *B01L 3/502715* (2013.01); *B01L 3/50273* (2013.01); *B01L 2200/027* (2013.01);
(Continued)

(58) Field of Classification Search
CPC .. B01L 3/502715; B01L 3/5027; B01L 3/502; B01L 3/50; B01L 3/50273; B01L 2200/0689; B01L 2200/06; B01L 2200/027; B01L 2200/02; B01L 2300/06; B01L 2300/08; B01L 2300/0832; B01L 2300/0883; B01L 2300/12; B01L 2400/0487; B01L 2400/04
(Continued)

(56) References Cited

U.S. PATENT DOCUMENTS 4,791,060 A * 12/1988 Chandler ......... G01N 33/54366
422/408
5,117,872 A    6/1992 Yie
(Continued)

FOREIGN PATENT DOCUMENTS

EP    1093854    4/2001
WO  WO-20080122908 A1  10/2008

*Primary Examiner* — Christine T Mui
(74) *Attorney, Agent, or Firm* — Fabian VanCott

(57) ABSTRACT

A sample test device is provided that includes a body having an insertion surface spaced apart from a distal end portion and a fluid manipulating assembly disposed in the distal end portion. A mixing receptacle is defined in the fluid manipulating assembly and provides a volume to mix a test mixture. A plunger is disposed in the body and creates a positive air pressure in the mixing receptacle when inserted into the body. A test die is disposed in the fluid manipulation assembly and a fluid path extends from the mixing receptacle to the test die. Activation of the plunger creates a positive pressure in the mixing receptacle to force the test mixture to flow from the mixing receptacle to the test die.

20 Claims, 12 Drawing Sheets

(52) U.S. Cl.
 CPC ... *B01L 2200/0689* (2013.01); *B01L 2300/06* (2013.01); *B01L 2300/0832* (2013.01); *B01L 2300/0883* (2013.01); *B01L 2300/12* (2013.01); *B01L 2400/0487* (2013.01)

(58) Field of Classification Search
 USPC .................................................. 422/69, 68.1
 See application file for complete search history.

(56) References Cited

U.S. PATENT DOCUMENTS

| | | | |
|---|---|---|---|
| 6,248,294 B1 | 6/2001 | Nason | |
| 7,507,374 B2 * | 3/2009 | Gould | A61B 10/0051 422/417 |
| 7,837,939 B2 | 11/2010 | Tung | |
| 8,216,832 B2 | 7/2012 | Battrell | |
| 8,894,946 B2 | 11/2014 | Nielsen | |
| 9,535,054 B2 | 1/2017 | Yuan | |
| 2007/0166198 A1 | 7/2007 | Sangha | |
| 2007/0244368 A1 | 10/2007 | Bayloff | |
| 2012/0167672 A1 | 7/2012 | Miller | |
| 2016/0116381 A1 | 4/2016 | Haupt | |
| 2017/0043334 A1 | 2/2017 | Khattak | |

* cited by examiner

TEST SAMPLE DEVICES AND METHODS

BACKGROUND

Current micro/mesofluidic test devices (e.g., Nucleic Acid Test) require electrical power systems to drive and regulate pressure within the test device to move the micro/mesofluids through the test device to a test die (e.g. chip). For example, the test devices require motor driven pistons and lead screws to accurately route reagents and test samples to various chambers for preparation and testing. The tooling required to perform the test needs to have well controlled motors, drive electronics, and power management. In addition, the electrical components required to route the reagents and test sample have high power requirements.

DETAILED DESCRIPTION

Disclosed herein is a manually operated example test sample device that creates a positive air pressure to force a fluid through the test sample device without the need for electrically powered systems to generate the positive air pressure. The example test device can be used in Nucleic Acid Tests including for example, DNA and RNA tests, etc. to detect and/or identify pathogens (e.g., virus, bacteria, etc.) in a test sample. The test device uses an efficient compressible fluid system (plunger and a compressible fluid (e.g., air)) to provide a controlled and consistent pressurized driving force to route a test mixture comprised of the test sample saturated with a test solution through channels defined in the device without the need for an electrical power system to drive and regulate the pressures.

By way of example, the test device includes a plunger having a test sample collection device disposed thereon with an O-ring that is urged into a corresponding receptacle of the test device containing a fluid such as air. Urging the plunger into the receptacle (a chamber) creates positive air pressure therein, which forces the test sample through one or more channels and to a test area (e.g., test die, test chip). In some examples, another test material (a fluidic test solution) may be injected into a mixing receptacle where it is mixed with the test sample to provide a test mixture. The pressure further causes the test mixture to travel through channel(s) to the test area. The diameter and tortuous shape of the channels restricts the fluid flow-rate of the test mixture thereby providing downstream flow control of the test mixture. The stored air pressure energy facilitates human activation of the plunger to drive the test sample and resulting test mixture to the test area and thus, mitigates the need for electrical equipment to apply a specific pressure at a specific rate.

Figure 1:
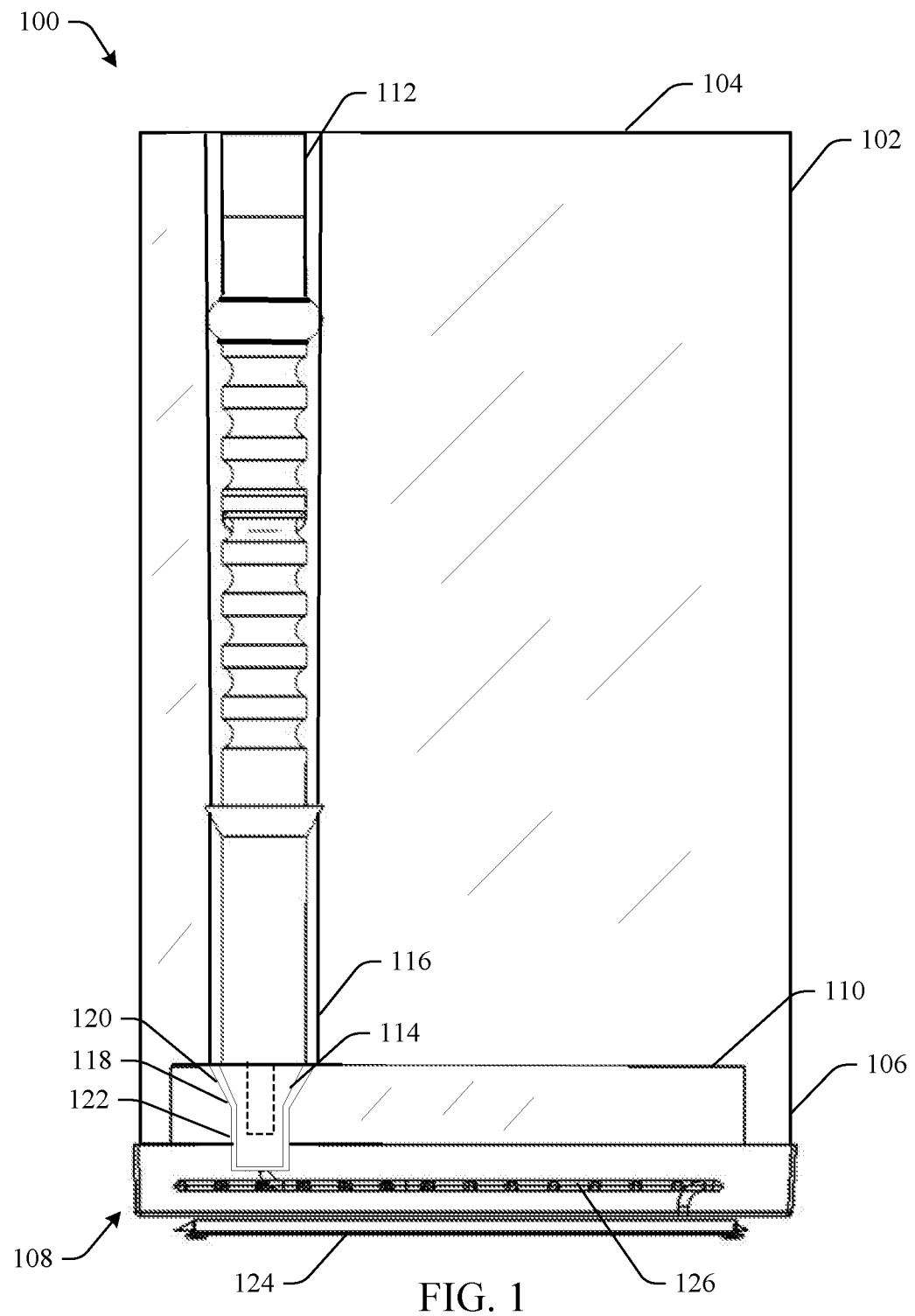
FIG. 1 illustrates a plan view of an example apparatus.

FIG. 1 is a plan view of an example apparatus 100 that includes a body 102 having an insertion surface 104 spaced apart from a distal end portion 106. A fluid manipulating assembly 108 is disposed in the distal end portion 106 of the body 102 and includes an interior surface 110. A plunger 112 slidably disposed in the body 102 and extending from the insertion surface 104 and terminating adjacent the fluid manipulating assembly 108. An absorbent compressible material 114 is attached to a distal end 116 of the plunger 112 and contains a test sample. A mixing receptacle 118 is defined in the fluid manipulating assembly 108 and includes a taper-shaped opening 120 and a cylindrical cavity 122 to facilitate extraction of the test sample from the absorbent compressible material 114. A test area (e.g., test die, test chip) 124 is disposed in the fluid manipulation assembly 108 and a fluid path 126 extends from the mixing receptacle 118 to the test area 124. Activation of the plunger 112 creates a positive pressure in the mixing receptacle 118 to force the test mixture to flow from the mixing receptacle 118 to the test area 124.

Figure 2:
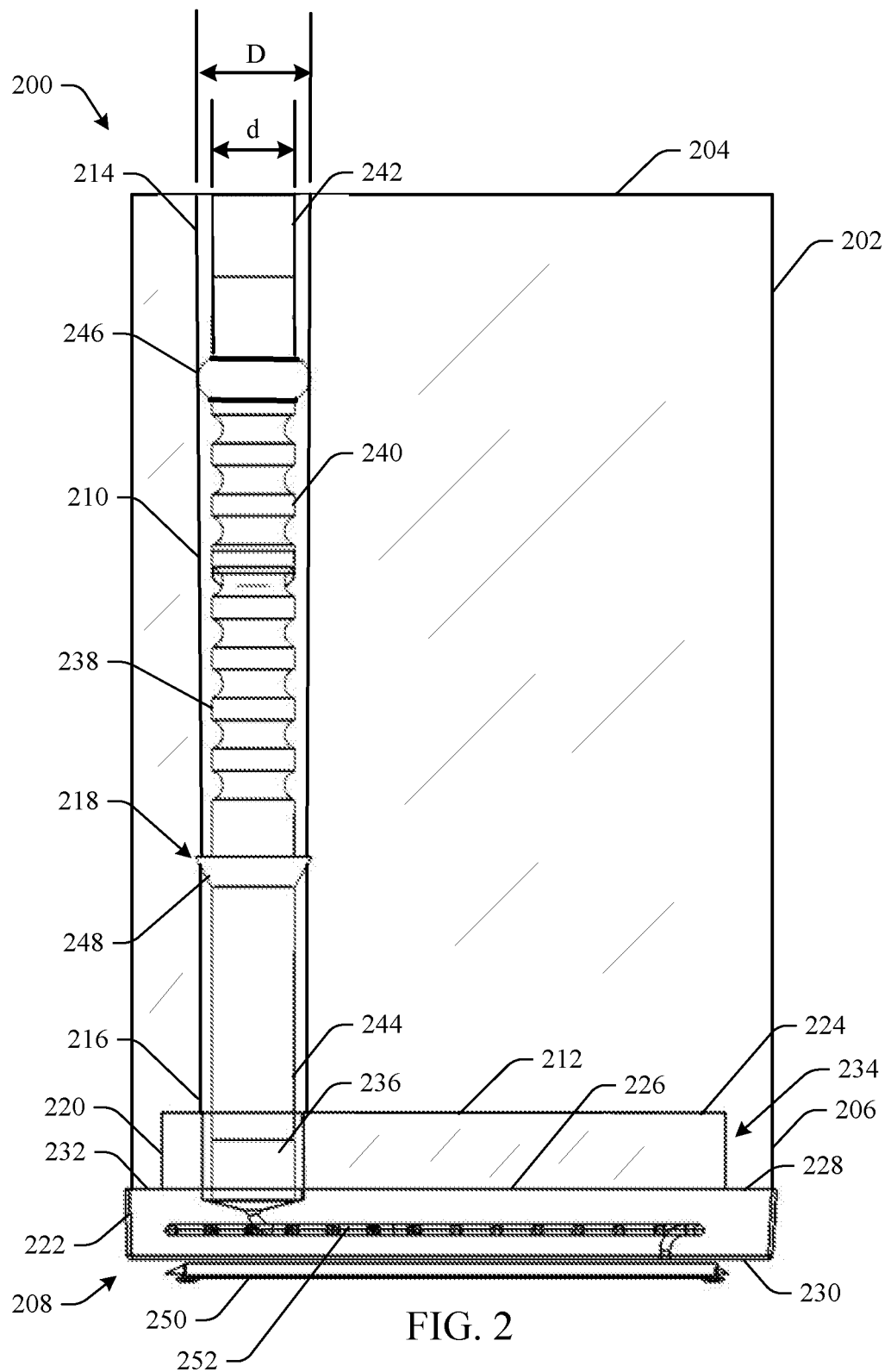
FIG. 2 illustrates a plan view of an example test sample device.

FIG. 2 is a plan view of an example test device 200. For example, the test device can be used in Nucleic Acid Test including for example, DNA and RNA tests, etc., as mentioned above. The sample test device 200 includes a body 202 having an insertion surface 204 spaced apart from a distal end 206 of the body 202. A base (fluid manipulating assembly) 208 is disposed in the distal end 206 of the body 202 and includes an interior surface 210. A chamber 212 is defined in the body 202 and receives a plunger described further below. The chamber 212 includes a proximate end 214 and a distal end 216 and extends from the insertion surface 204 of the body 202 to the interior surface 212 of the base 208, thus defining a receptacle having a volume dimensioned to receive the plunger therein. The chamber 212 has a diameter D and a locking recess 218 defined circumferentially around its interior surface at a location between the proximate end 214 and the distal end 216.

Figure 3:
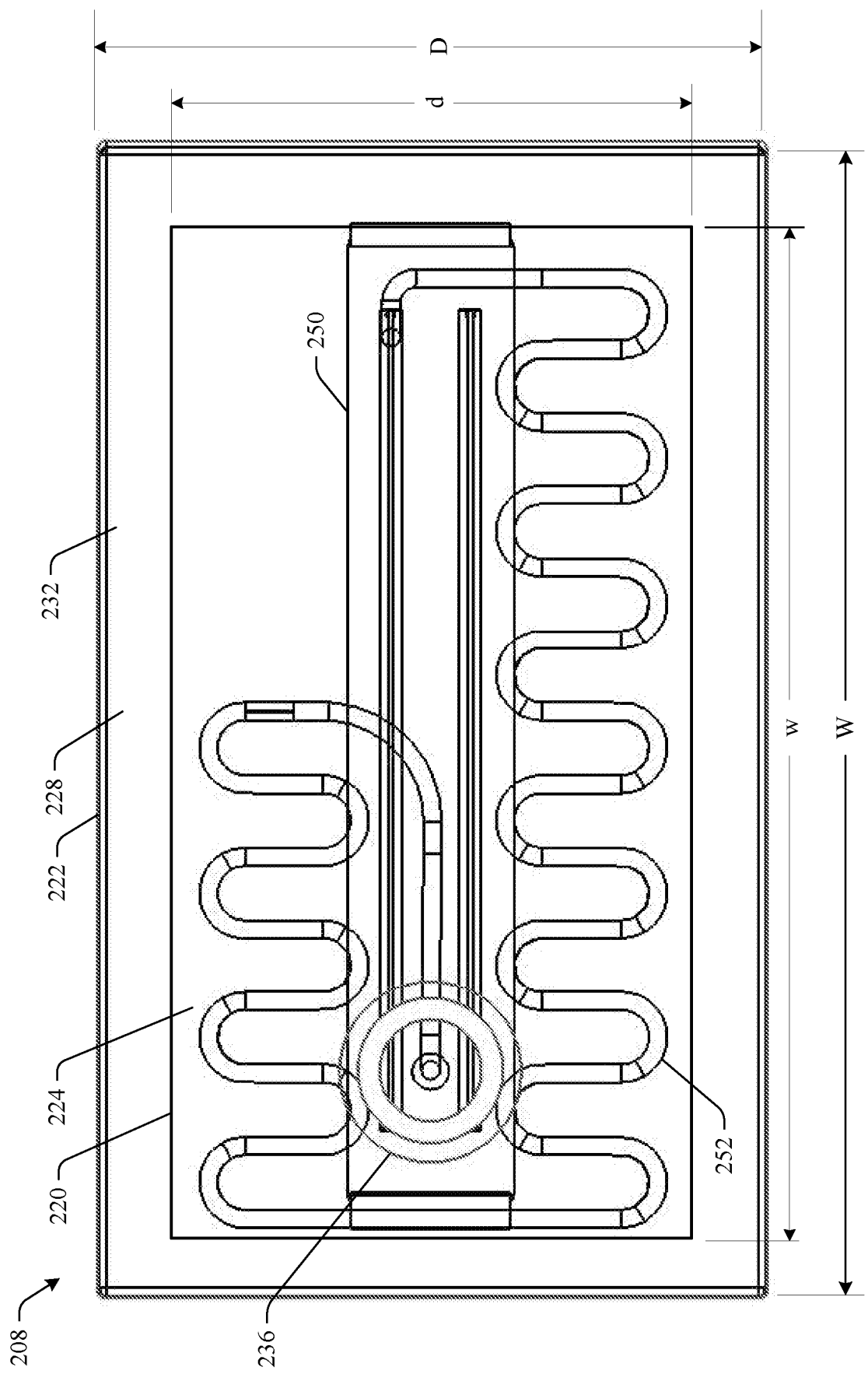
FIG. 3 illustrates a top view of a fluid manipulating assembly.

Still referring to FIG. 2 and also to FIG. 3, FIG. 3 is a top view of the base 208. In one example, the base 208 includes a proximal (mixing) layer 220 disposed on a distal (transport) layer 222. The proximal layer 220 has spaced apart opposing surfaces 224 and 226 where side surface 226 is a contact surface. Similarly, the distal layer 222 has opposing side surfaces 228 and 230 where 228 is a support surface. The proximal layer 220 is disposed on the distal layer 222 such that the contact surface 226 of the proximal layer 220 resides on the support surface 228 of the distal layer 222. The distal layer 222 has a width W wider and a depth D deeper than a width w and a depth d of the proximal layer 220 such that a lip (shoulder) 232 is formed on side surface 228 of the distal layer 222. The base 208 is inserted into a recess 234 defined in the distal end 206 of the body 202 such that the proximal layer 220 is disposed inside the body 202 and an end face formed around a perimeter of the recess 234 is hermetically sealed to the lip 232. In another example, the proximal 220 and distal 222 layers can have a similar sized length and width and the body 202 can be hermetically sealed to the proximal layer 220. In still yet another example, the body 202 and the base 208 can be formed as an integrated (monolithic) unit.

A mixing receptacle 236 is defined in the base 208 adjacent the distal end 216 of the chamber 212. The mixing receptacle 236 has a defined volume that receives a test solution that, when combined with a test sample, forms a test mixture.

A plunger 238 is slidably disposed in the chamber 212 and includes a shaft 240 having a proximate end 242 and a distal end 244. The plunger 238 has a diameter d that is less than the diameter D of the chamber 212. When fully inserted into the body 202, the distal end 244 of the plunger 238 terminates adjacent the mixing receptacle 236. A pliant sealing device (e.g., an O-ring) 246 is disposed around an intermediate location between the proximate 242 and distal 244 ends of the shaft 240. The pliant sealing device 246 has a diameter that is greater than the diameter D of the chamber 212 and facilitates the creating and maintaining of the positive air pressure in the chamber 212 and the mixing receptacle 236 explained further below. The plunger 238 further includes a locking device 248 disposed around the shaft 240 between the proximate end 242 and the distal end 244 of the shaft 240. The locking device 248 has a diameter greater than the diameter d of the shaft 240 and greater than the diameter D of the chamber 212. When the plunger 238 is fully activated (fully inserted into the body 202), the locking device 248 engages the locking recess 218 to prevent removal of the plunger 238.

A test area (e.g., test die, test chip) 250 is disposed adjacent the side surface 230 of the distal layer 222 of the base 208. A fluid path (e.g., channel) 252 is defined in the base 208 that fluidly connects the mixing receptacle 236 and the test area 250. When the plunger 238 is activated, the pliant sealing device 246 seals air inside the chamber 212 between the pliant sealing device 246 and the mixing receptacle 236 creating positive air pressure in the chamber 212 and the mixing receptacle 236. As the plunger 238 is moved further towards the mixing receptacle 236, the positive air pressure in the chamber 212 and the mixing receptacle 214 forces the test mixture to flow from the mixing receptacle 236 through the fluid path 252 to the test area 250. As illustrated in FIG. 2, the fluid path 252 can have a tortuous shape that facilitates a controlled flow of the test solution from the fluid path 252 and to the test area 250.

Figure 4:
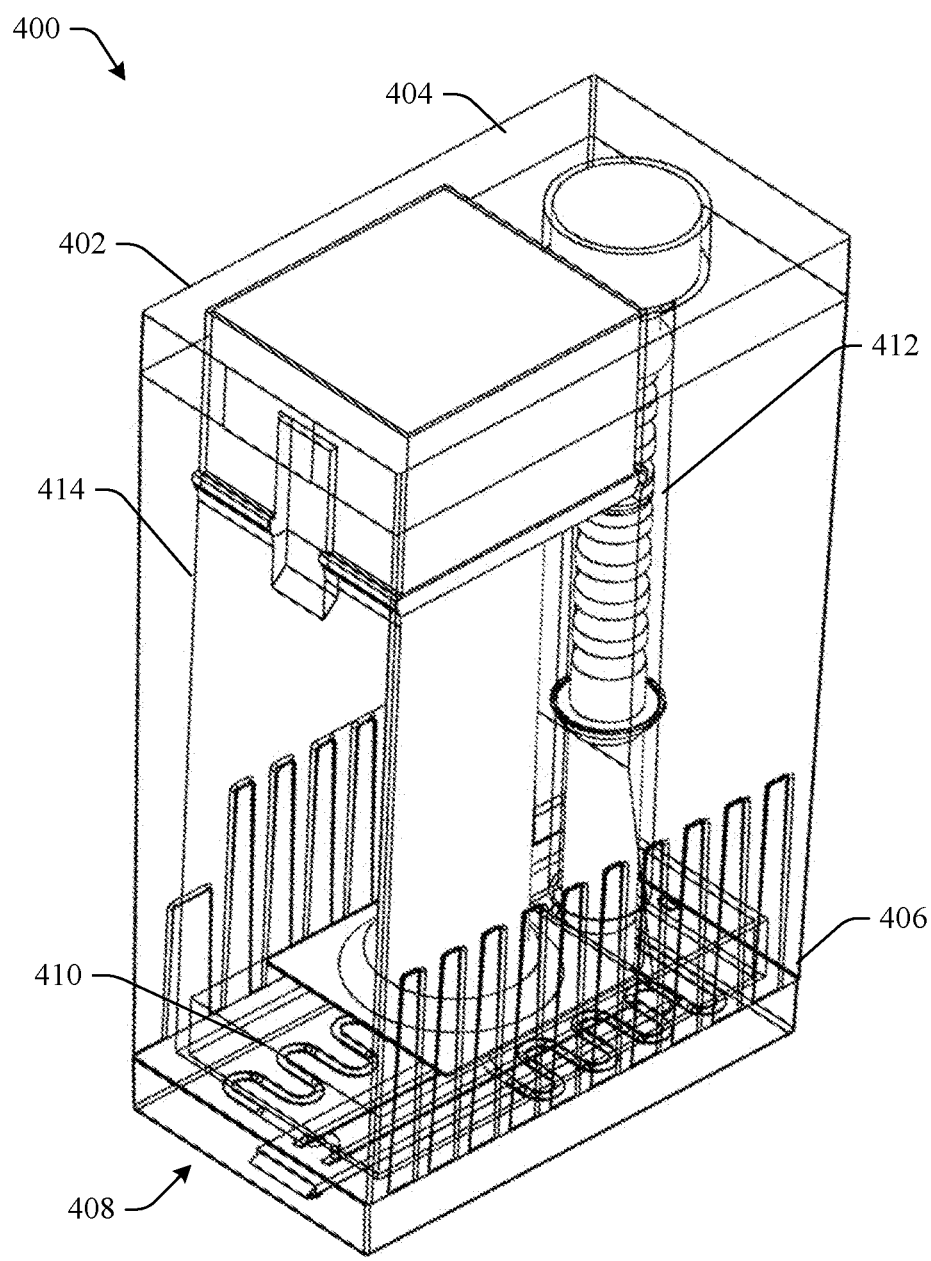
FIG. 4 illustrates a perspective view of another example of a test sample device.
Figure 5:
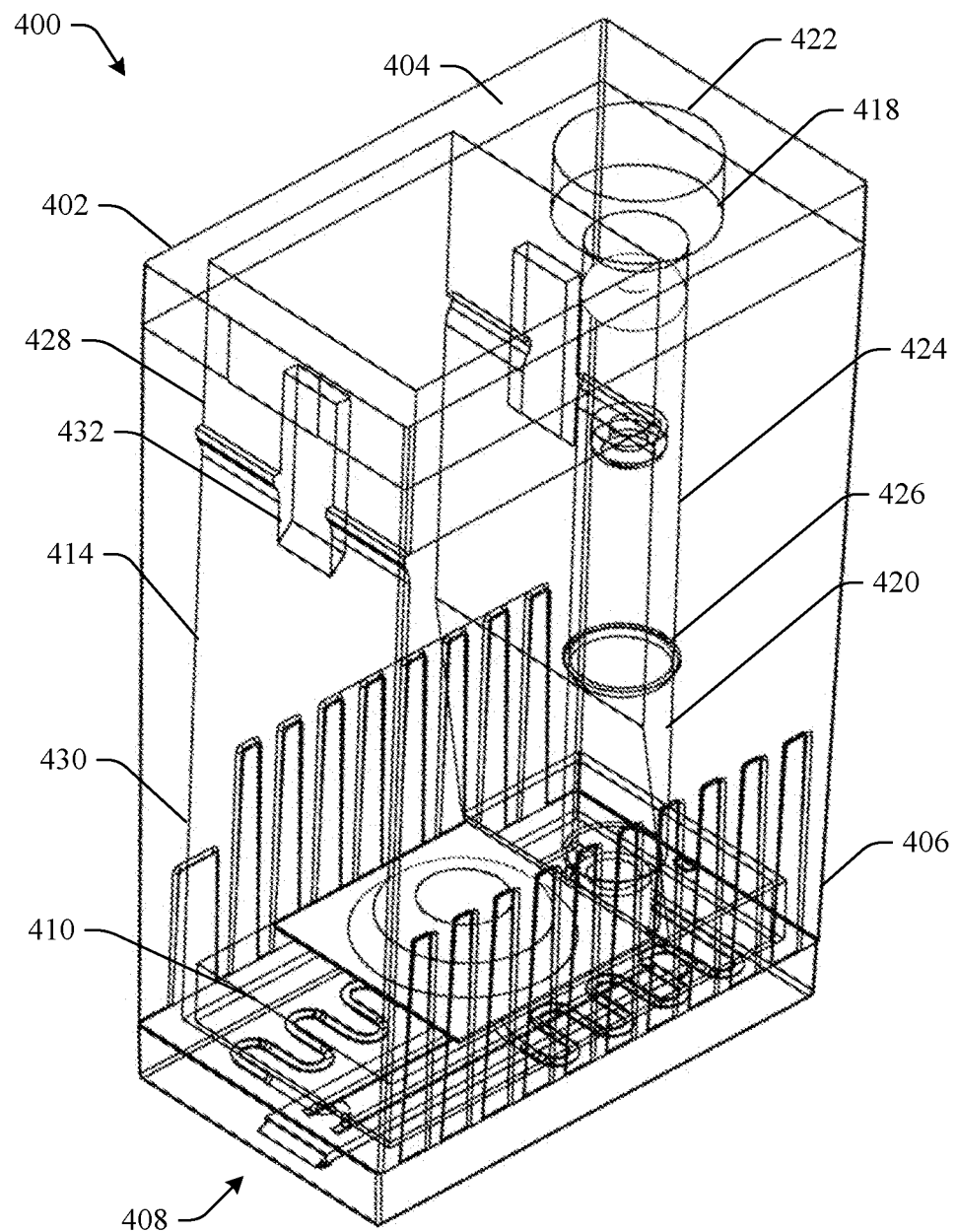
FIG. 5 illustrates a perspective view of the test sample device of FIG. 4 without a plunger and an actuator.
Figure 6:
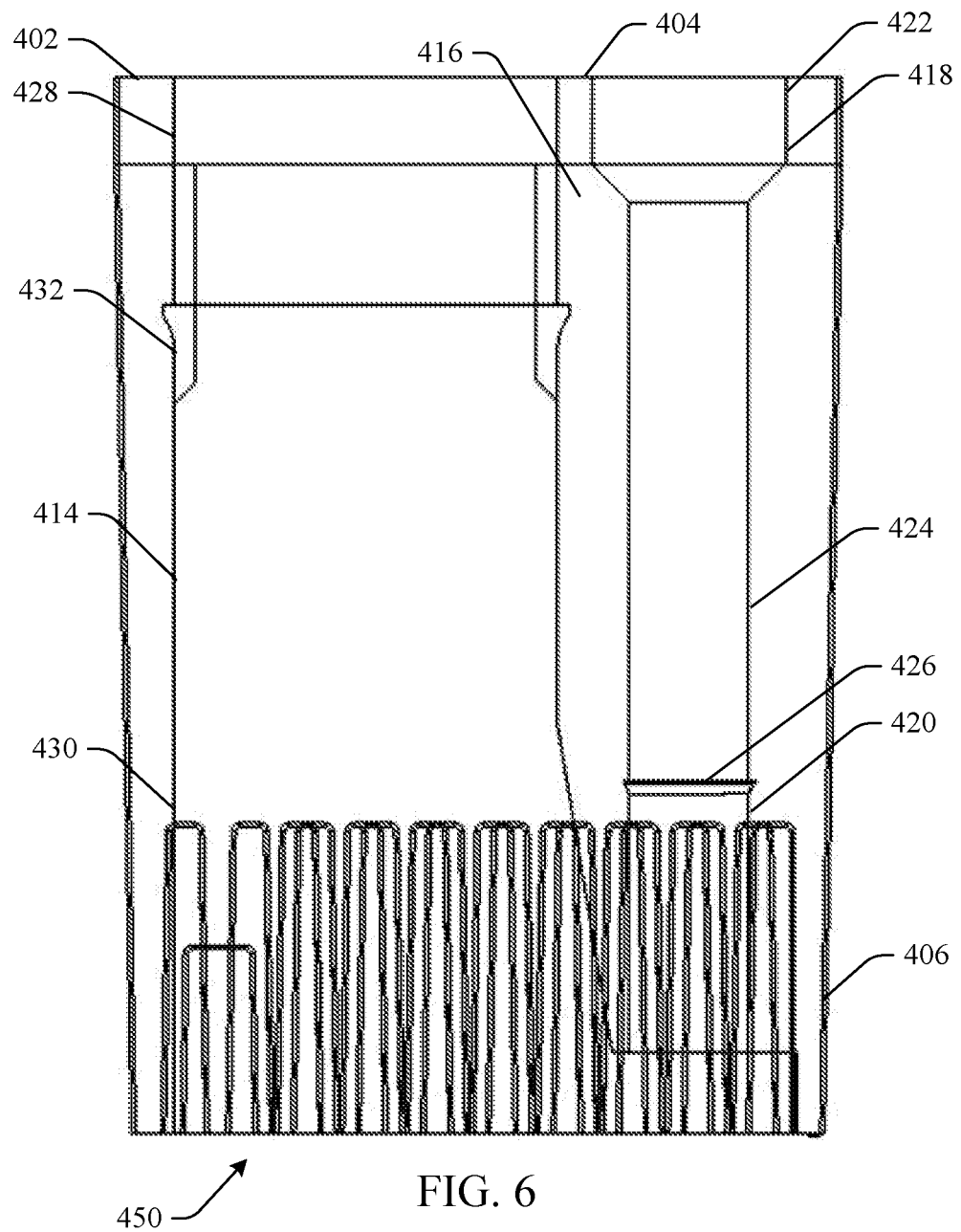
FIG. 6 is a plan view of a body of the example test sample device of FIG. 4.

FIGS. 4-11 illustrate another example of a test device 400, such as can be used in Nucleic Acid Tests including for example, DNA and RNA tests etc., as mentioned above. Referring to FIGS. 4-6, the sample test device 400 includes a body 402 having an insertion surface 404 spaced apart from a distal end 406 of the body 402. A base (fluid manipulating assembly) 408 described further below is disposed in the distal end 406 of the body 402 and includes an interior surface 410. A plunger chamber 412 is defined in the body 402 and receives a plunger, described further below. An actuator chamber 414 is defined in the body 402 adjacent to the plunger chamber 412 and receives an actuator described further below. An intermediate barrier 416 separates the plunger chamber 412 from the actuator chamber 414.

The plunger chamber 412 includes a proximate end 418 and a distal end 420, and extends from the insertion surface 404 of the body 402 to the interior surface 410 of the base 408. The proximate end 418 of the plunger chamber 412 includes a wide portion 422 having a substantially constant diameter. The wide portion 422 tapers to a narrowed portion 424 whereby the narrowed portion 424 has a substantially constant diameter that is smaller than the diameter of the wide portion 422. The narrowed portion 424 extends to the distal end 420 of the plunger chamber 412. A locking recess 426 is defined circumferentially around an interior surface of the narrow portion 424 at an intermediate location between the proximate end 418 and the distal end 420.

The actuator chamber 414 includes a proximate end 428 and a distal end 430, and extends from the insertion surface 404 of the body 402 to the interior surface 410 of the base 408. Locking recesses 432 are defined in side surfaces of the actuator chamber 414 that lock the actuator in place when actuated. In one example, the actuator chamber 414 can have a substantially constant width or diameter. In another example, the actuator chamber 414 can vary in width or diameter based on a shape of the actuator.

Figure 7:
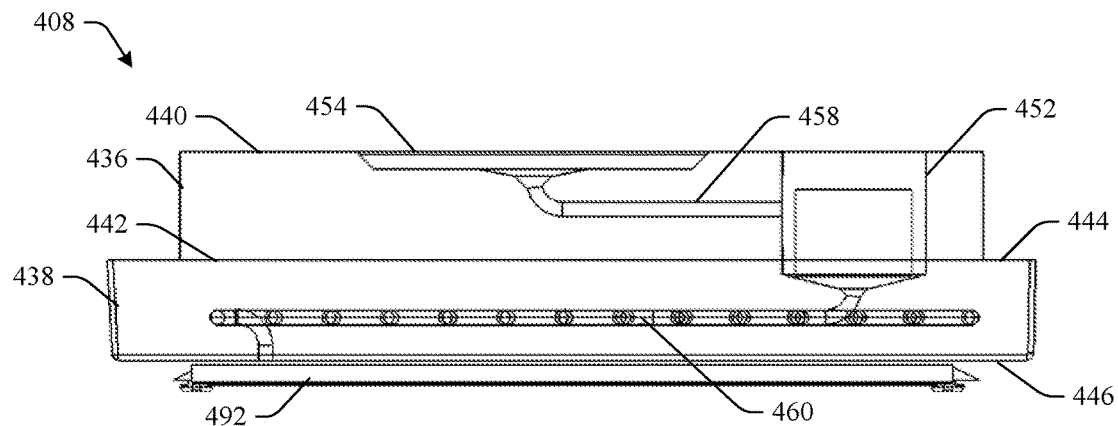
FIGS. 7 and 8 are side and top view illustrations respectively of a fluid manipulating assembly.
Figure 8:
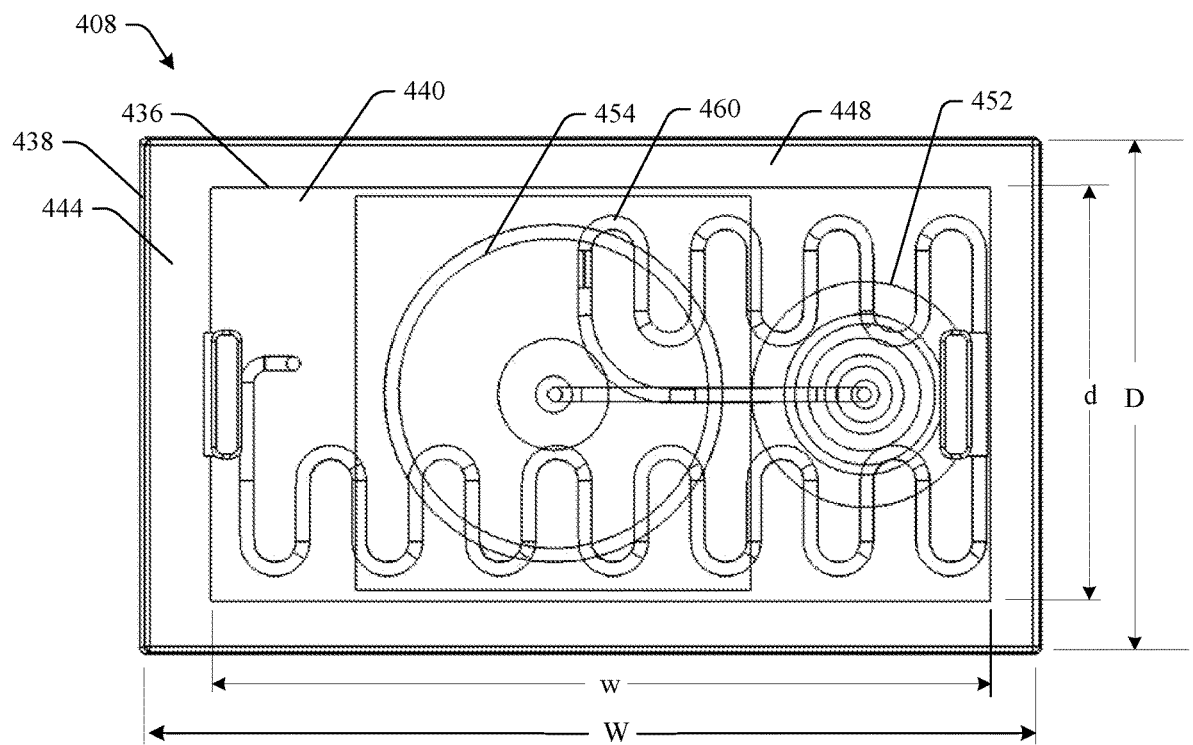

FIGS. 7 and 8 are illustrations of a plan view and a top view of the base 408, respectively. In one example, the base 408 includes a proximal (mixing) layer 436 disposed on a distal (transport) layer 438. The proximal layer 436 has spaced apart opposing side surfaces 440 and 442 where side surface 442 is a contact surface. Similarly, the distal layer 438 has spaced apart opposing side surfaces 444 and 446 where side surface 444 is a support surface. The proximal layer 436 is disposed on the distal layer 438 such that the contact surface 442 of the proximal layer 436 is disposed on the support surface 444 of the distal layer 438.

The distal layer 438 has a width W wider and a depth D deeper than a width w and a depth d of the proximal layer 436 such that a lip 448 is formed on the support side surface 444 of the distal layer 438. The base 408 is inserted into a recess 450 defined in the distal end 406 of the body 402 such that the proximal layer 436 is disposed inside the body 402 and an end face formed around a perimeter of the recess 450 is hermetically sealed to the lip 448. In another example, the proximal 436 and distal 438 layers can have a similar sized length and width and the body 402 can be hermetically sealed to the proximal layer 436. In still yet another example, the body 402 and the base 408 can be an integrated (monolithic) unit.

Still referring to FIGS. 7 and 8, a mixing receptacle 452 is defined in the base 408 adjacent the distal end 420 of the plunger chamber 412. For example, a fluid reservoir 454 is defined in the side surface 440 of the proximal layer 436 adjacent to the actuator chamber 414 and receives a test solution from a frangible package 456 (e.g., a blister package—see FIG. 9) disposed on the side surface 440 of the proximal layer 436. A fluid channel 458 is defined in the base 408 that provides a fluid connection between the fluid reservoir 454 and the mixing receptacle 452. When the frangible package 456 is ruptured, the test solution pools into the fluid reservoir 454 and travels through the fluid channel 458 to the mixing receptacle 452. In the mixing receptacle, the test solution is mixed (combined) with a test sample to form a test mixture. A fluid path 460 is defined in the distal layer 438 of the base 408 and provides a fluid connection from the mixing receptacle 452 to a test area described further below. The fluid path 460 can have a tortuous shape that facilitates a controlled flow of the test mixture from the mixing receptacle 452 to the test area.

Figure 9:
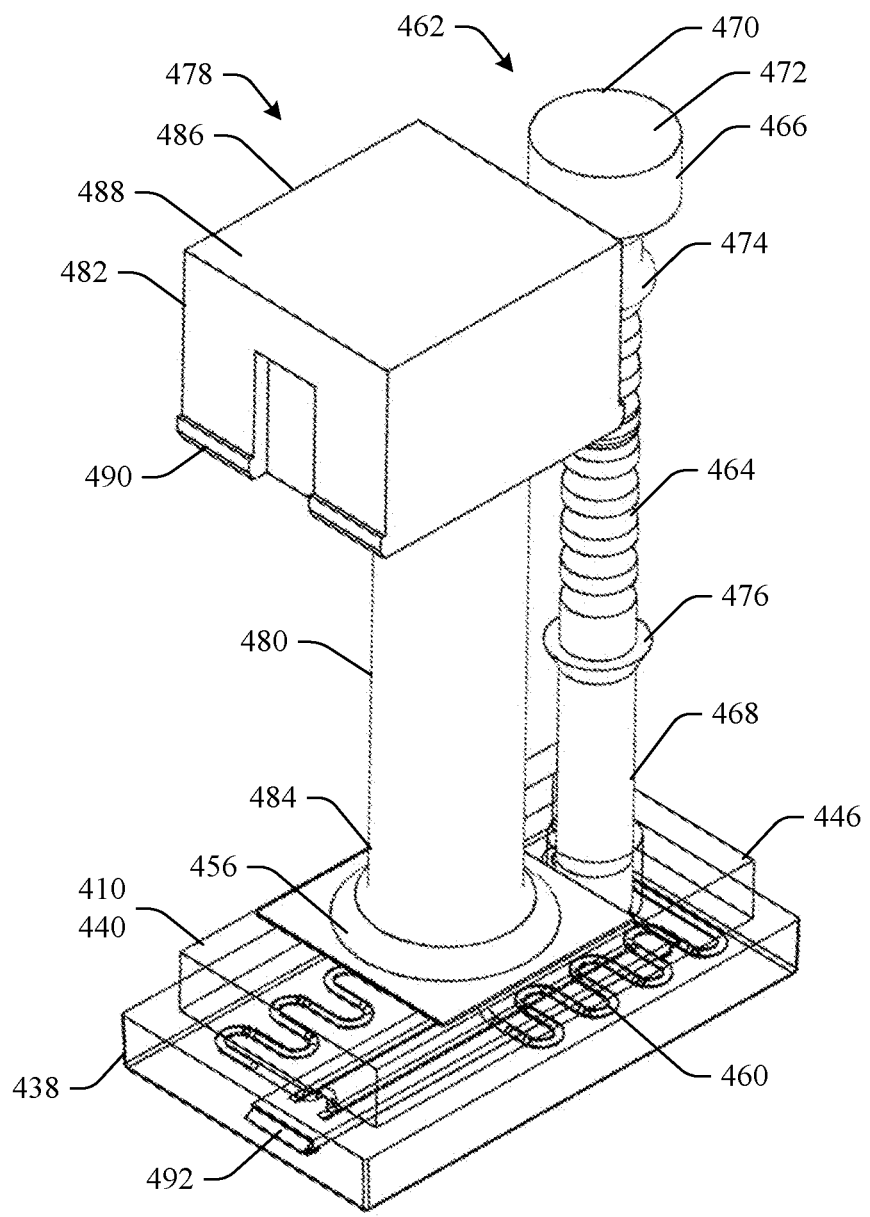
FIGS. 9 and 10 are perspective and plan views of the example test sample device of FIG. 4 without the body.
Figure 10:
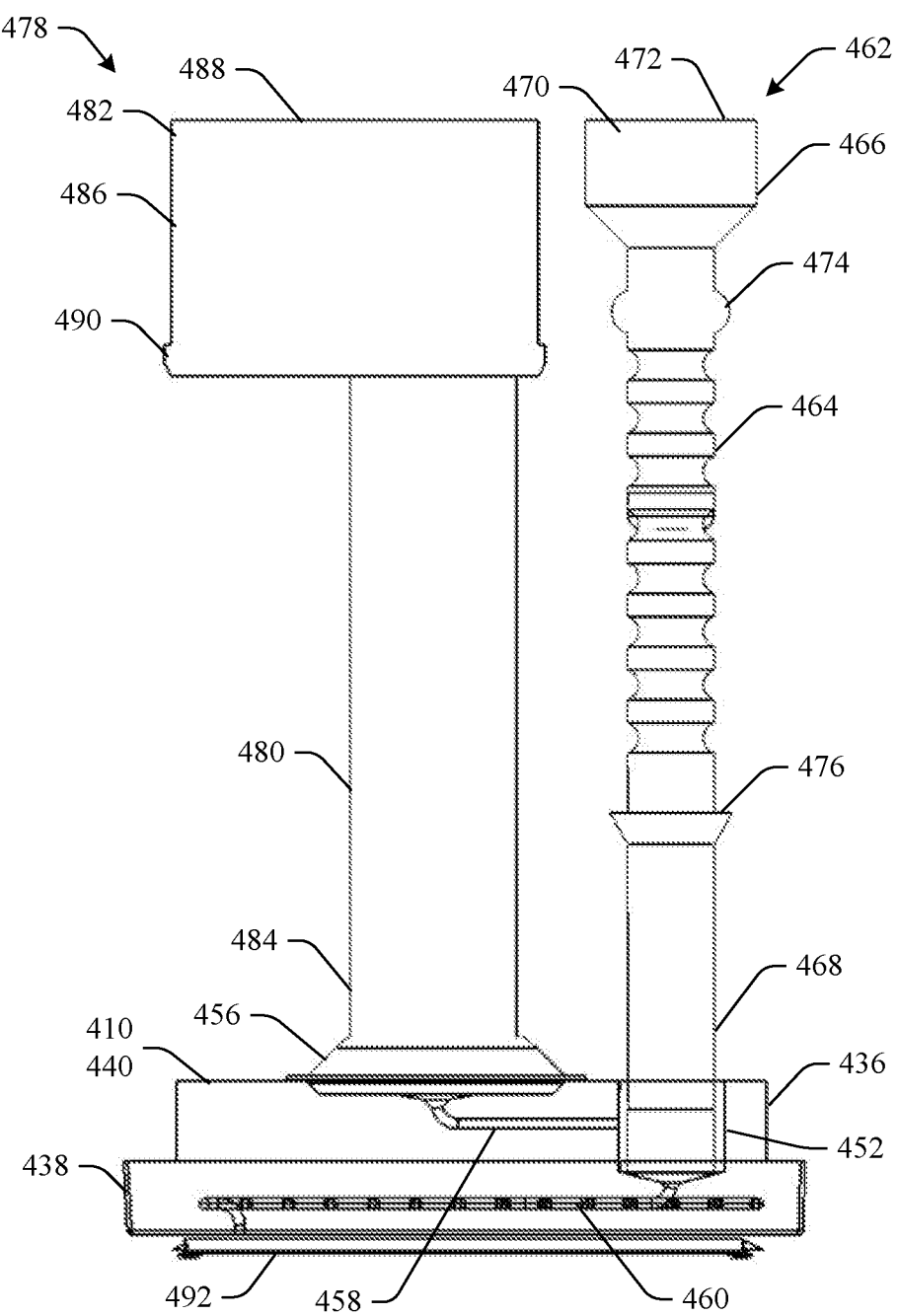

FIGS. 9 and 10 illustrate a perspective view and a plan view of the test device 400, respectively, without the body 402. A plunger 462 is slidably disposed in the plunger chamber 412 and includes a shaft 464 having a proximate end 466 and distal end 468. An activator 470 is disposed at the proximate end 466 of the shaft 464. The shaft 464 of the plunger 462 has a diameter that is less than the diameter of the narrow portion 424 of the plunger chamber 412. When fully inserted into the body 402, the distal end 468 of the plunger 462 terminates adjacent the mixing receptacle 452 and a top surface 472 of the activator 470 is substantially flush with the insertion surface 410 of the body 402.

A pliant sealing device (e.g., O-ring) 474 is disposed around an intermediate location between the proximate 466 and distal 468 ends of the plunger 462. The pliant sealing device 474 has a diameter that is greater than the diameter of the narrow portion 424 of the plunger chamber 412 and facilitates the creation of the positive air pressure in the plunger chamber 412 and the mixing receptacle 452 explained further below. The plunger 462 further includes a locking device 476 disposed around the shaft 464 between the proximate end 466 and the distal end 468 of the plunger 462. The locking device 476 has a diameter greater than the diameter of the shaft 466 and greater than the diameter of the narrow portion 424 of the plunger chamber 412. When the plunger 462 is fully activated (fully inserted into the body 402), the locking device 476 engages the locking recess 426 to prevent removal of the plunger 462.

Still referring to FIGS. 9 and 10, an actuator 478 is slidably disposed in the actuator chamber 414 and includes a shaft 480 having a proximate end 482 and a distal end 484. An actuation part 486 is disposed at the proximate end 482 of the shaft 480. When the actuator 478 is actuated (e.g., fully inserted into the body 402), a top surface 488 of the actuation part 486 is substantially flush with the insertion surface 410 of the body 402 and the distal end 484 of the shaft 480 contacts and thereby ruptures the frangible package 456. In response to rupturing (e.g., penetrating) the frangible package 456, a test solution is released to enable flow to the mixing receptacle 452. The actuation part 486 includes locking projections 490 that engage the locking recess 432 defined in the actuator chamber 414 to lock the actuator in the body 402 when the actuator 478 is actuated.

A test area (e.g., test die, test chip) 492 is disposed adjacent the side surface 446 of the distal layer 438 of the base 408. When the plunger 462 is activated, the pliant sealing device 474 seals air inside the plunger chamber 412 between the pliant sealing device 474 and the mixing receptacle 452 creating positive air pressure in the plunger chamber 412 and the mixing receptacle 452. As the plunger 462 is moved further towards the mixing receptacle 452, the positive air pressure in the plunger chamber 412 and the mixing receptacle 452 forces the test mixture (a combination of the test sample and test solution) to flow from the mixing receptacle 452 through the fluid path 460 to the test area 492. As mentioned above, the fluid path 460 can have a tortuous shape that facilitates a controlled flow of the test mixture that flows from the fluid path 460 to the test area 492.

Figure 11:
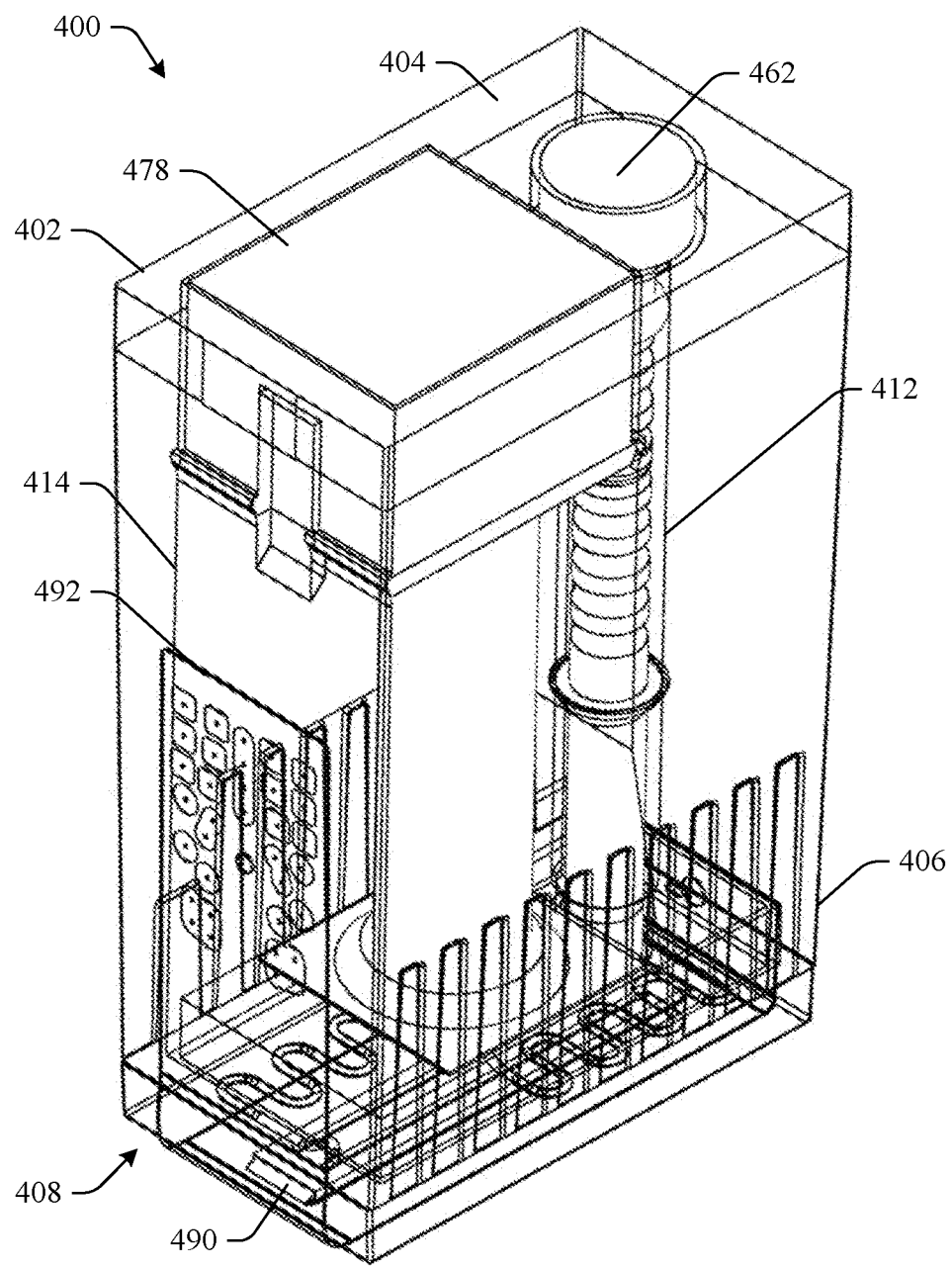
FIG. 11 illustrates a perspective view of another example of a test sample device that includes an analyzer.

Referring to FIG. 11, after the test mixture reaches the test area 492, the test device 400 can be connected to an analyzer via an interface 494. The analyzer can read the test area 490 to determine is any substances such as pathogens (e.g., virus, bacteria, etc.) are present.

Figure 12A:
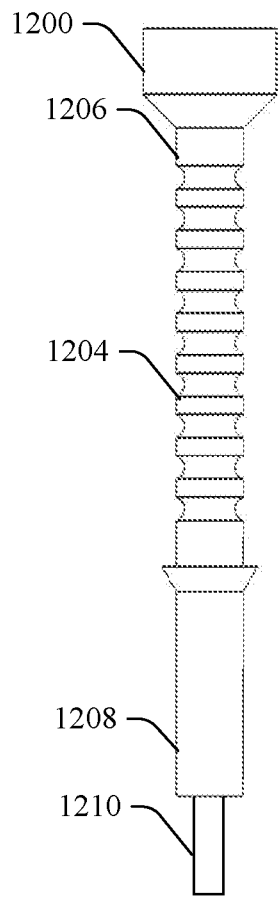
FIGS. 12A and 12B are plan view illustrations of an example plunger without and with a sample collection device respectively.
Figure 12B:
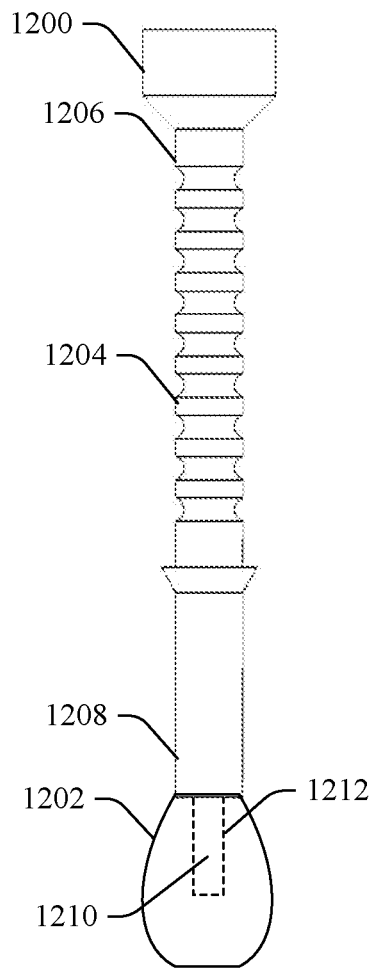

FIGS. 12A and 12B are illustrations of an example plunger 1200 having an attached sample collection device 1202 that can be used in the example test devices disclosed herein. Like features of the example plunger 1200 to those disclosed herein will not be repeated. The collection device 1202 is comprised of an absorbent compressible material (e.g., cotton swab) to facilitate collection of a test sample.

The plunger 1200 includes a shaft 1204 having a proximate end 1206 and a distal end 1208. An attachment part 1210 extends from the distal end 1208 of the shaft 1204 to terminate in a distal end thereof. The attachment part 1210 has a diameter that is less than the diameter of the distal end 1208 of the plunger from which it coaxially extends. The collection device 1202 has a cavity 1212 defined therein that receives the attachment part 1210 and is adhered to the attachment part 1210 (e.g., by an adhesive) to facilitate collection of the test sample. The diameter of the attachment part 1210 is such that when the collection device 1202 is fully inserted into the mixing receptacle described below, the collection device 1202 is able to compress or squeeze to facilitate extraction of the test mixture.

Figure 13:
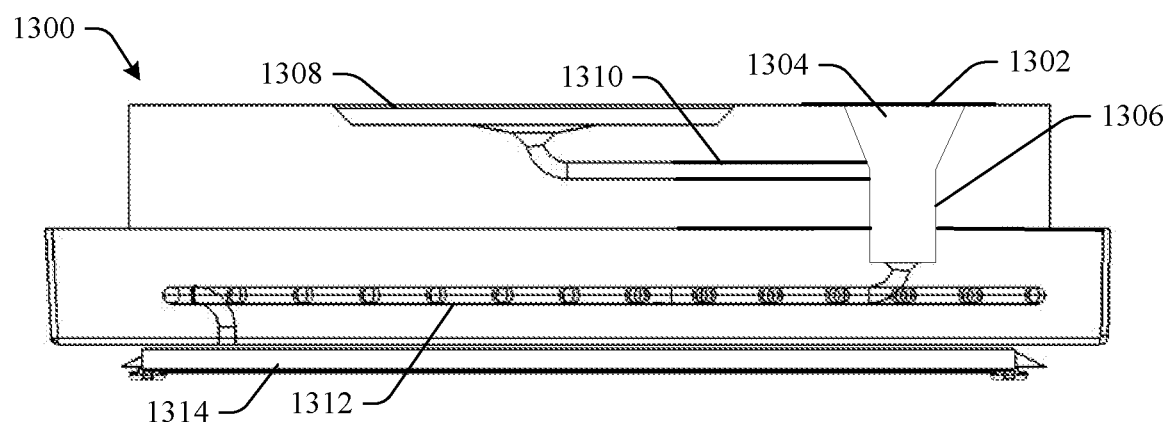
FIG. 13 is an example fluid manipulation assembly having a mixing receptacle that extracts a test mixture from the collection device.

FIG. 13 is a plan view illustration of an example fluid manipulating assembly 1300 having a mixing receptacle 1302 defined therein that facilitates efficient extraction of a test mixture from the test sample collection device 1202. Like features of the fluid manipulating assembly 1300 to those disclosed herein will not be repeated. The mixing receptacle 1302 has a width or diameter that is less than a width or diameter of the collection device 1202. In one example, the mixing receptacle 1302 can include a tapered opening 1304 transitioning into a cylindrical cavity 1306, which has a width or diameter that is less than the width or diameter of the collection device 1202. The width or diameter of the cylindrical cavity 1306 is greater than the width or diameter of the attachment part 1210 to enable its insertion into the cylindrical cavity 1306. The tapered opening 1304 facilitates entry of the collection device 1202 into the cylindrical cavity 1306 of the mixing receptacle 1302.

By way of example, as the plunger 1200 is partially inserted into the test sample device, the collection device 1202 enters the tapered opening 1304. A test solution in response to rupturing the frangible package (e.g., blister pack) described above travels from the fluid reservoir 1308 to the mixing receptacle 1302 via the fluid channel 1310. The test solution saturates the collection device 1202 and mixes with the test sample to form the test mixture. As the plunger 1200 is fully inserted into the test device, the collection device 1202 enters the cylindrical cavity 1306 upon which the cylindrical cavity 1306 compresses (squeezes) the collection device 1202 such that the width or diameter of the collection device 1202 collapses thereby extracting the test mixture from the collection device 1202. As a result, positive pressure created by the plunger 1200 in the mixing receptacle 1302 forces the test mixture through a fluid path 1312 to a test area (e.g., test die, test chip) 1314.

In another example, as the collection device 1202 enters the tapered opening 1304, a volume of the test sample on the collection device 1202 is forced from the collection device 1202 into the mixing receptacle 1302. The extracted volume of the test sample further mixes with a volume of test solution that has traveled from a fluid reservoir 1308 to the mixing receptacle 1302 via a fluid channel 1310 to form the test mixture in response rupturing a frangible package (e.g., blister pack) containing the test solution. Positive pressure created by the plunger 1200 in the mixing receptacle 1302 when the plunger 1200 is fully inserted into the test sample device forces the test mixture through the fluid path 1312 to the test area 1314.

Integrating the collection device with the plunger reduces the number of parts required to collect the test sample and perform the test. Another advantage is that the taper-shaped opening, the cylindrical cavity, and the absorbent compressible material of the collection device increases the extraction efficiency of the test mixture from the collection device. Still further, a size and shape of the collection device and the mixing receptacle can be matched to increase the extraction efficiency.

Figure 14:
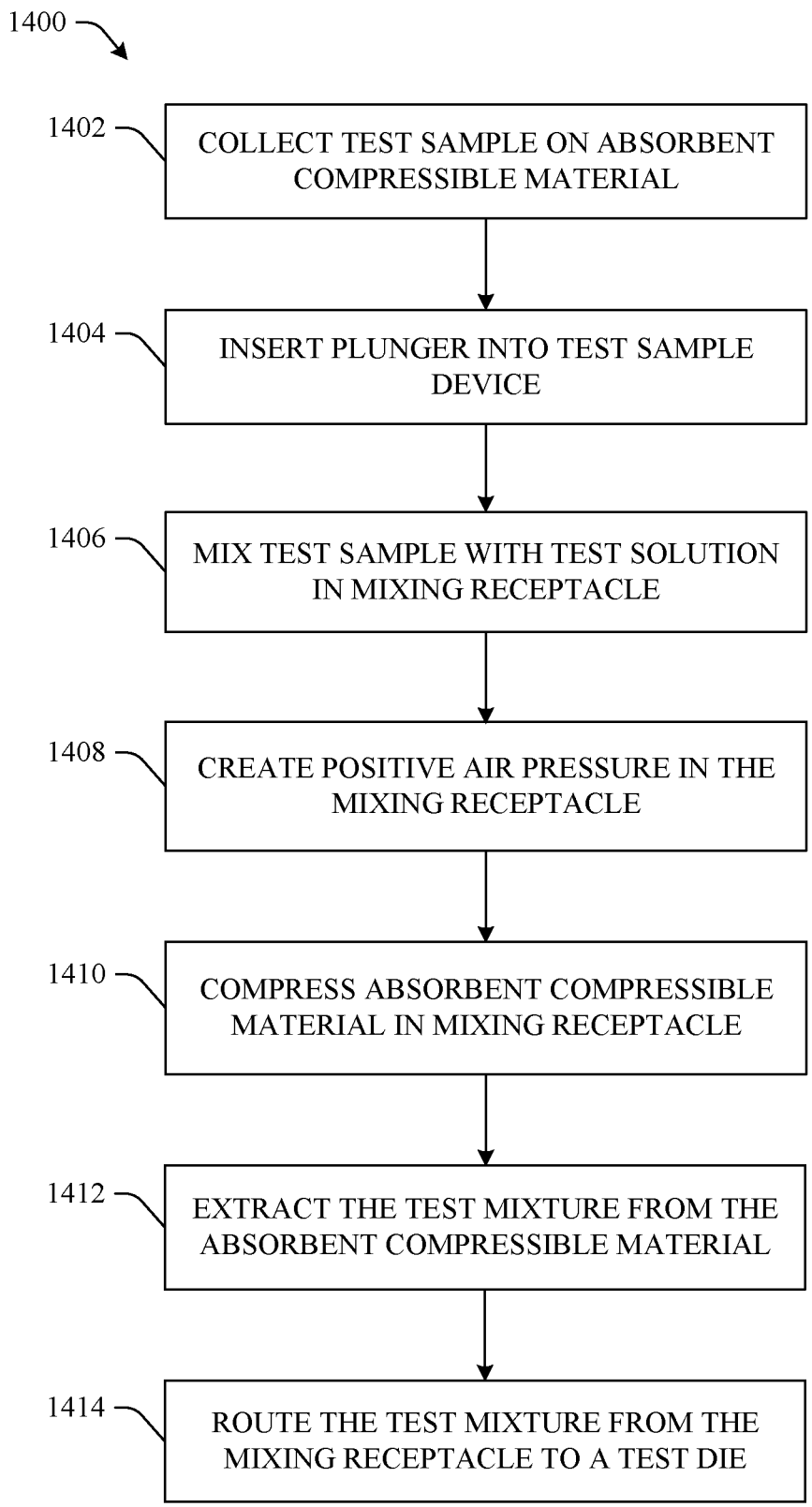
FIG. 14 is a flow diagram of an example method of collecting and extracting a test mixture in a test device.

FIG. 14 represents an example method 1400 of collecting and extracting a test sample in a test sample device (e.g., device 100, 200, 400). At 1402, a sample is collected with an absorbent compressible material (e.g., cotton swab 114, 1202). At 1404, a plunger (e.g., plunger 112, 238, 462, 1200) is inserted into the test sample device (e.g., device 100, 200, 400) such that the absorbent compressible material (e.g., cotton swab 114, 1202) is inserted into a tapered opening (e.g., tapered opening 120, 1304) of a mixing receptacle (e.g., receptacle 118, 238, 452, 1302). At 1406, the test sample is mixed with a test solution in the mixing receptacle (e.g., receptacle 118, 238, 452, 1302) to form a test mixture. At 1408, positive air pressure is created in the mixing receptacle (e.g., receptacle 118, 238, 452, 1302). At 1410, the absorbent compressible material (e.g., cotton swab 114, 1202) disposed on a distal end (e.g., distal end 116, 244, 468, 1208) of the plunger (e.g., plunger 112, 238, 462, 1200) is compressed in the mixing receptacle (e.g., receptacle 118, 238, 452, 1302) such that a width or diameter of the absorbent compressible material (e.g., cotton swab 114, 1202) collapses. At 1412, the test mixture is extracted from the absorbent compressible material (e.g., cotton swab 114, 1202). At 1414, the test mixture is routed in a fluid path (e.g., channel 126, 252, 460, 1312) from the mixing receptacle (e.g., receptacle 118, 238, 452, 1302) to a test area (e.g., test die 124, 250, 492, 1314).

Described above are examples of the subject disclosure. It is, of course, not possible to describe every conceivable combination of components or methodologies for purposes of describing the subject disclosure, but one of ordinary skill in the art may recognize that many further combinations and permutations of the subject disclosure are possible. Accordingly, the subject disclosure is intended to embrace all such alterations, modifications and variations that fall within the spirit and scope of the appended claims. In addition, where the disclosure or claims recite "a," "an," "a first," or "another" element, or the equivalent thereof, it should be interpreted to include one or more than one such element, neither requiring nor excluding two or more such elements. Furthermore, to the extent that the term "includes" is used in either the detailed description or the claims, such term is intended to be inclusive in a manner similar to the term "comprising" as "comprising" is interpreted when employed as a transitional word in a claim. Finally, the term "based on" is interpreted to mean at least based in part.

What is claimed is:

1. An apparatus comprising:
    a body having an insertion surface spaced apart from a distal end portion;
    a fluid manipulating assembly disposed in the distal end portion;
    a plunger slidably disposed in the body extending from the insertion surface and terminating adjacent the fluid manipulating assembly;
    an absorbent compressible material attached to a distal end of the plunger to contain a test sample;
    a mixing receptacle defined in the fluid manipulating assembly, the mixing receptacle having a taper-shaped opening and a cylindrical cavity to facilitate extracting the test sample from the absorbent compressible material and to provide a volume to mix a test mixture; and
    a test area in the fluid manipulation assembly, a fluid path extending from the mixing receptacle to the test area and activation of the plunger creates a positive pressure in the mixing receptacle to force the test mixture, including an extracted portion of the test sample, to flow from the mixing receptacle to the test area.

2. The apparatus of claim 1, the absorbent compressible material having a diameter, the cylindrical cavity having a diameter that is less than the diameter of the absorbent compressible material.

3. The apparatus of claim 1, in response to a distal end of the plunger entering the taper-shaped opening, the test sample being extracted to mix with a test solution and form the test mixture.

4. The apparatus of claim 1, further comprising a plunger chamber to receive the plunger and extending from the insertion surface to an interior surface of the fluid manipulating assembly, the plunger chamber including a wide portion having a diameter and a narrow portion having a diameter that is less than the diameter of the wide portion.

5. The apparatus of claim 4, the plunger including a shaft having a shaft diameter less than the diameter of the narrow portion of the plunger chamber, an activator disposed at a proximate end of the shaft, and an attachment portion disposed at a distal end of the shaft, the attachment portion extending into the mixing receptacle when the plunger is activated.

6. The apparatus of claim 5, the plunger further including a pliant sealing device disposed around the proximate end of the shaft, the pliant sealing device having a diameter greater than the diameter of the narrow portion of the plunger chamber.

7. The apparatus of claim 1, further comprising:
    an actuator disposed in the body; and
    an actuator chamber to receive the actuator therein to provide for actuation of the actuator from the actuator chamber extending from the insertion surface to an interior surface of the fluid manipulating assembly.

8. The apparatus of claim 7, further comprising:
    a frangible package disposed on the interior surface of the fluid manipulating assembly adjacent to the actuator chamber, the actuator moveable within the body to contact and rupture the frangible package in response to be actuated;
    a fluid test solution path extending from the frangible package to the mixing receptacle; and
    a test die attached to the test area to receive the test mixture in response to activation of the plunger.

9. A test device comprising:
    a body having an insertion surface spaced apart from a distal end portion;
    a fluid manipulating assembly disposed in the distal end portion;
    a frangible package disposed on fluid manipulating assembly spaced from the mixing receptacle;
    a plunger slidably disposed in the body extending from the insertion surface and terminating adjacent the fluid manipulating assembly;
    an absorbent compressible material attached to a distal end of the plunger to contain a test sample;
    a mixing receptacle defined in the fluid manipulating assembly, the mixing receptacle having a taper-shaped opening and a cylindrical cavity to facilitate extracting the test sample from the absorbent compressible material and to provide a volume to mix a test mixture; and
    a test die disposed in the fluid manipulation assembly, a fluid path extending from the mixing receptacle to the test area and activation of the plunger creates a positive pressure in the mixing receptacle to force the test mixture, including an extracted portion of the test sample, to flow from the mixing receptacle to the test die.

10. The test device of claim 9, the absorbent compressible material having a diameter, the cylindrical cavity having a diameter that is less than the diameter of the absorbent compressible material.

11. The test device of claim 9, in response to a distal end of the plunger entering the taper-shaped opening, the test sample being extracted to mix with a test solution and form the test mixture.

12. The test device of claim 9, further comprising a plunger chamber to receive the plunger, the plunger chamber extending from the insertion surface of the body to an interior surface of the fluid manipulating assembly, the plunger chamber including a wide portion having a diameter and a narrow portion having a diameter that is less than the diameter of the wide portion.

13. The test device of claim 12, the plunger comprising:
a shaft extending between proximate and distal ends, the shaft having a shaft diameter less than the diameter of the narrow portion of the plunger chamber;
an attachment portion disposed at the distal end of the shaft, the attachment portion extending into the mixing receptacle when the plunger is activated; and
a pliant sealing device disposed around the shaft at a location intermediate the proximate end and the distal end, the pliant sealing device having a diameter greater than the diameter of the narrow portion of the plunger chamber.

14. The test device of claim 9, further comprising
an actuator disposed in the body, the actuator being moveable within the body to contact and rupture the frangible package in response to be actuated; and
an actuator chamber to receive the actuator therein to provide for actuation of the actuator, the actuator chamber extending from the insertion surface to an interior surface of the fluid manipulating assembly.

15. A method comprising:
collecting a test sample with an absorbent compressible material;
inserting a plunger into a test device so the absorbent compressible material enters a tapered opening of a mixing receptacle;
mixing the test sample with a test solution in the mixing receptacle to form a test mixture;
creating a positive air pressure in the mixing receptacle in response to inserting the plunger;
compressing the absorbent compressible material disposed on a distal end of the plunger in a cylindrical cavity of the mixing receptacle;
extracting the test mixture from the absorbent compressible material in response to compressing the absorbent compressible material; and
routing the test mixture via a fluid path of the test device from the mixing receptacle to a test area in response to the positive air pressure.

16. The apparatus of claim 4, wherein:
the plunger chamber comprises a locking recess defined circumferentially around its interior surface; and
the plunger comprises a locking device to engage with the locking recess to prevent removal of the plunger.

17. The apparatus of claim 1, wherein the absorbent compressible material has a cavity defined therein to receive an attachment part of the plunger.

18. The apparatus of claim 1, wherein the fluid manipulating assembly has a mixing layer disposed on a distal layer.

19. The apparatus of claim 18, wherein:
the distal layer is wider and deeper than the mixing layer; and
the fluid manipulating assembly is into a recess in the distal end portion of the body.

20. The apparatus of claim 18, wherein the fluid path is disposed in the distal layer.

\* \* \* \* \*